US00PP14442P29

(12) United States Plant Patent
Gerdts et al.

(10) Patent No.: US PP14,442 P2
(45) Date of Patent: Jan. 6, 2004

(54) NECTARINE TREE NAMED 'BURNECTTEN'

(50) Latin Name: *Prunus persica var. nucipersica*
Varietal Denomination: Burnectten

(75) Inventors: Timothy J. Gerdts, Kingsburg, CA (US); John K. Slaughter, Clovis, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 10/318,765

(22) Filed: Dec. 13, 2002

(51) Int. Cl.[7] ..... A01H 5/00
(52) U.S. Cl. ..... Plt./190
(58) Field of Search ..... Plt./190

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of nectarine tree (*Prunus persica,* var. *nucipersica*) denominated varietally as 'Burnectten', and which produces attractively colored yellow-fleshed, clingstone nectarines which are mature for harvesting and shipment approximately May 5 to May 11 under the ecological conditions prevailing in the San Joaquin Valley of central California.

1 Drawing Sheet

BACKGROUND OF THE NEW VARIETY

The present invention relates to a new, novel and distinct variety of nectarine tree, *Prunus persica* var. *nucipersica*, and which has been denominated varietally as 'Burnectten'.

ORIGIN

The present variety of nectarine tree resulted from an on-going program of fruit and nut tree breeding. The purpose of this program is to improve the commercial quality of deciduous fruit and nut varieties and rootstocks by creating and releasing promising selections of prunus, malus and regia species. To this end we make both controlled and hybrid cross pollinations each year in order to produce seedling populations from which improved progenies are evaluated and selected.

The seedling 'Burnectten' was originated by us from a population of seedlings grown in our experimental orchards located near Fowler, Calif. The seedlings, grown on their own roots, were the result of a controlled cross of the yellow-fleshed, early ripening, open pollinated seedling of the peach tree 'Rich Lady' (U.S. Plant Pat. No. 7,290), which was used as the pollen parent, and the low chilling time nectarine tree, 'SunCoast', (unpatented) and which was used as the seed parent. One seedling, which is the present variety, exhibited especially desirable characteristics, and was subsequently designated as E45.049. This promising variety was marked for subsequent observation. After the 1999 growing season, the new variety was selected for advanced evaluation and repropagation.

ASEXUAL REPRODUCTION

Asexual reproduction of the new and distinct variety of nectarine tree was accomplished by budding the new variety to 'Nemaguard' Rootstock (non-patented). This was performed by us in our experimental orchard which is located near Fowler, Calif. Subsequent evaluations have shown those asexual reproductions run true to the original tree. All characteristics of the original tree, and its fruit, were established and appear to be transmitted through succeeding asexual propagations.

SUMMARY OF THE VARIETY

'Burnectten' is a new and distinct variety of nectarine tree, which is of moderately-large size, and which has vigorous growth. The new variety is also a regular and productive bearer of relatively large, firm, yellow fleshed, clingstone fruit which has good flavor and eating quality. This new and novel tree has a relatively low chilling requirement of approximately 350 hours. Still further, this tree also produces relatively uniformly sized fruit throughout the tree with a high degree of red skin coloration, and firm flesh. The fruit of this new tree also appears to have good handling and shipping qualities. Moreover, the 'Burnectten' nectarine tree bears fruit that is ripe for commercial harvesting and shipment on approximately May 5 to May 11. In relative comparison with the 'Sun Coast' nectarine tree which is the seed parent, the new variety ripens about 20 or more days earlier at the same geographical location.

BRIEF DESCRIPTION OF THE DRAWING

The accompanying drawing, which is provided, is a color photograph of the present variety. It depicts two whole mature fruit and one fruit dissected in substantially the equatorial plane to expose the flesh and the pit. Additionally the photograph displays a characteristic twig bearing typical leaves. Also a pit is displayed with the flesh removed. The external coloration of the fruit as shown is sufficiently matured for harvesting and shipment. The colors are as nearly true as is reasonably possible in a color representation of this type. Due to chemical development, processing and printing, the color of the leaves and fruit depicted in these photographs may or may not be accurate when compared to the actual specimen. For this reason, future color references should be made to the color plates (Royal Horticultural Society) and descriptions provided hereinafter.

DETAILED DESCRIPTION

Referring more specifically to the pomological details of this new and distinct variety of nectarine tree, the following has been observed during the fourth fruiting season under the ecological conditions prevailing at orchards located near the town of Fowler, county of Fresno, state of California. All major color code designations are by reference to The R.H.S. Color Chart (Fourth Edition) provided by The Royal Horticultural Society of Great Britain.

Tree:

*Size.*—Generally. — Considered medium large when compared to other common commercial nectarine cultivars ripening in the early season of maturity. The tree of the present variety was pruned to a height of approximately 272.0 cm to 290.0 cm at maturity.

*Vigor.*—Moderately vigorous. The present variety grew from about 118.0 cm to 167.0 cm in height during the first growing season. The variety was pruned to a height of approximately 104.7 cm in the first dormant season and primary scaffolds were then selected for desired tree structure.

*Productivity.*—Productive. Fruit set varies from at least about three times the desired crop load. Fruit set is spaced by thinning to develop the remaining fruit into the desired market size. The variety typically sets heavy crops. The number of fruit set varies with climatic conditions and prevailing cultural practices during the bloom period and is therefore not distinctive of the variety.

*Bearer.*—Regular. Fruit set has been heavy and thinning was necessary during the past 4 years.

*Form.*—Upright, and pruned to a vase shape.

*Density.*—Medium dense. It has been discovered that pruning the branches from the center of the tree to obtain a resulting vase shape allows for air movement and appropriate amounts of sunlight to enhance fruit color and renewal of fruiting wood throughout the tree.

*Hardiness.*—The present tree was grown and evaluated in USDA Hardiness Zone 9. Winter chilling requirements are approximately 300 hours below 7.0 degrees C. The variety appears to be hardy under typical central San Joaquin Valley climatic conditions.

Trunk:

*Diameter.*—Approximately 12.7 cm in diameter when measured at a distance of approximately 15.24 cm above the soil level, at the end of the fourth growing season.

*Bark texture.*—Considered moderately rough, with numerous folds of papery scarfskin being present.

*Lenticels.*—Numerous flat, oval lenticels are present. Lenticels are somewhat less prominent than is typically observed in other commercial nectarine varieties. The lenticels range in size from approximately 3.0 to about 4.0 millimeters in width, and from about 1.0 to about 2.0 millimeters in height.

*Lenticel color.*—Considered an orange brown, (RHS Greyed Orange Group N167 C).

*Bark coloration.*—Variable, but it is generally considered to be grey-brown, (RHS Grey Brown Group N199 B).

Branches:

*Size.*—Considered medium for the variety.

*Diameter.*—Average as compared to other varieties. The branches have a diameter of about 5.9 centimeters when measured during the fourth year after grafting.

*Surface texture.*—Average, and appearing furrowed on wood which is several years old.

*Crotch angles.*—Primary branches are considered variable and between about 44 to 52 degrees from the horizontal axis. This characteristic is not considered distinctive of the variety, however.

*Current season shoots.*—Surface texture — Substantially glabrous.

*Internode length.*—Approximately 1.9 to about 2.2 cm.

*Color of mature branches.*—Medium brown, (RHS Grey Brown Group N199 C).

*Current seasons shoots.*—Color — Light green, (RHS Yellow Green Group 144 B). The color of new shoot tips is considered a bright and shiny green (RHS Yellow Green Group 144 A).

Leaves:

*Size.*—Considered medium, to medium-small for the species. Leaf measurements have been taken from vigorous, upright, current-season growth at approximately mid-shoot.

*Leaf length.*—Approximately 132.0 to about 161.0 millimeters.

*Leaf width.*—Approximately 29.0 to about 37.0 millimeters.

*Leaf base shape.*—Slightly oblique relative to the leaf longitudinal axis.

*Leaf form.*—Lancelolate.

*Leaf tip form.*—Acuminate.

*Leaf color.*—Dark green, (approximately RHS Green Group 136 B).

*Leaf texture.*—Glabrous.

*Lower surface.*—Medium green, (RHS Green Group 139 B).

*Leaf venation.*—Pinnately veined.

*Mid-vein.*—Color. — Light yellow green, (RHS Green Group 141 D).

*Leaf margins.*—Slightly undulating.

*Form.*—Considered crenate, occasionally doubly crenate.

*Uniformity.*—Considered generally uniform.

*Leaf petioles.*—Size — Considered medium-short. Length — About 7.0 to about 10.0 mm. Diameter — About 1.5 to about 2.0 mm. Color — Pale green, (RHS Yellow Green Group 144 C).

*Leaf glands.*—Size — Considered small for the species; about 1.0 mm in height, and about 1.0 mm in width. Number — Generally one per side, occasionally two per side. Type — Reniform, and considered reasonably unappressed relative to the petiole margin. Color — Orange brown, (RHS Greyed Orange Group163 A).

*Leaf stipules.*—Size — Medium small for the variety. Number — Typically 2 per leaf bud, and up to 6 per shoot tip. Form — Lanceolate in form and having a serrated margin. Color — Green, (RHS Green Group 141 B) when young, but graduating to a brown color, (RHS Greyed Orange group N172 A) with advancing senescence. The stipules are considered to be early deciduous.

Flowers:

*Flower buds.*—Generally — The floral buds, depending upon the stage of development are approximately 8.0 millimeters wide; and about 12.0 millimeters long; conic in form; and slightly appressed relative to the bearing shoot.

*Flower buds.*—Color — The bud scales are reddish-brown, (approximately RHS Greyed Purple Group 183 A). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress and therefore this information is not available.

*Date of first bloom.*—Feb. 18, 2002.

*Blooming time.*—Considered early season in relative comparison to most commercial nectarine cultivars grown in the central San Joaquin Valley. Date of full bloom was observed on Feb. 21, 2002. The date of bloom varies slightly with climatic conditions and prevailing cultural practices.

*Duration of bloom.*—Approximately 8 days. This characteristic varies slightly with climatic conditions.

*Flower type.*—The variety is considered to have a showy type flower.

*Flower size.*—Flower diameter at full bloom is approximately 41.0 to about 45.0 millimeters.

*Bloom quantity.*—Considered very abundant.

*Flower bud frequency.*—Normally 2 or more appear per node.

*Petal size.*—Generally — Considered medium-large for the species. Length — Approximately 18.0 to about 21.0 millimeters. Width — Approximately 17.0 to about 20.0 millimeters.

*Petal form.*—Broadly ovate.

*Petal count.*—Nearly always 5.

*Petal texture.*—Glabrous.

*Petal color.*—Light pink when young, (RHS Red Purple Group 73 B) and darkening with advancing senescence and exposure to sunlight to a medium to dark pink, (RHS Red Purple Group N66 C).

*Fragrance.*—Slight.

*Petal claw.*—Form — The claw is considered truncate, and has a medium size when compared to other varieties. Length — Approximately 7.0 to about 9.0 millimeters. Width — Aproximately 6.0 to about 8.0 millimeters.

*Petal margins.*—Generally considered variable, from nearly smooth, to moderately undulate and ruffled, especially apically.

*Petal apex.*—Generally — The petal apices generally appear entire at the tip.

*Flower pedicel.*—Length — Considered medium-long, and having an average length of approximately 3.0 to about 4.0 millimeters. Diameter — Considered average, approximately 2.0 millimeters. Color — A medium brown, (RHS Grey Orange Group 177 C).

*Floral nectaries.*—Color — A Dull orange red, (RHS Red Group 43 B).

*Calyx.*—Surface Texture — Generally glabrous. Color — A dull red, (approximately RHS Greyed Purple Group 183 B).

*Sepals.*—Surface Texture — The surface has a short, fine pubescent texture. Size — Average, and ovate in form. Color — A dull red, (approximately RHS Greyed Red Group 183 D).

*Anthers.*—Generally — Average to above average in length. Color — Red to reddish-orange dorsally, (approximately RHS Greyed Red Group 180 A).

*Pollen production.*—Pollen is abundant, and has a yellow color, (approximately RHS Yellow Orange Group 17 A).

*Filaments.*—Size — Variable in length, approximately 13.0 to about 17.0 millimeters in length. Color — Considered a pinkish-white, (RHS Red Purple Group 62 D).

*Pistil.*—Number — Usually 1, occasionally 2, rarely 3. Generally — Average in size. Length — Approximately 19.0 to about 22.0 millimeters including the ovary. Color — Considered a very pale green, (approximately RHS Yellow Green Group 151 D). Surface Texture — The variety has a long glabrous pistil.

Fruit:

*Maturity when described.*—Firm ripe condition (shipping ripe). Date of first picking — May 5, 2002. Date of last picking — May 12, 2002. The date of harvest varies slightly with climatic conditions.

*Size.*—Generally — Considered medium large for early season fruit, and uniform.

*Average cheek diameter.*—Approximately 69.0 to about 75.0 millimeters.

*Average axial diameter.*—Approximately 67.0 to about 72.0 millimeters.

*Typical weight.*—Approximately 248.0 grams. This is highly dependent upon cultural practices and therefore is not distinctive of the variety.

*Fruit form.*—Generally — Moderately oblate. The fruit is generally uniform in symmetry.

*Fruit suture.*—Shallow, and extending from the base to apex. No apparent callousing or stitching exists along the suture line.

*Suture.*—Color — The background color appears to be a yellow to golden yellow (approximately RHS Yellow Orange Group 20 A), and occasionally some red coloration is evident (approximately RHS Red Group 46 A).

*Ventral surface.*—Form — Slightly indented.

*Apex.*—Rounded. Usually indented.

*Base.*—Retuse.

*Stem cavity.*—Rounded to slightly rounded in the suture plane. Average depth of the stem cavity is about 1.20 cm. Average width is about 2.43 cm.

*Fruit skin.*—Thickness — Considered medium in thickness, and tenacious to the flesh. Texture — Glabrous. Taste — Non-astringent. Tendency to crack — None observed.

*Color.*—Blush Color — This red blush color is variable from a reddish orange, (approximately RHS Orange Red Group N34 B) to a dark red, (approximately RHS Red Group 46 B). Blush color ranges from about 75% to about 95% of the fruit surface depending upon sunlight exposure and the prevailing growing conditions. Ground Color — Yellow orange, (approximately RHS Yellow Orange Group 21 C).

*Fruit stem.*—Medium in length, approximately 7.0 to about 8.5 millimeters. Diameter — Approximately 2.0 to about 3.0 millimeters. Color — Pale yellow-green, (approximately RHS Yellow Green Group 144 D).

*Flesh.*—Ripens — Evenly. Texture — Firm, and dense. Considered non-melting. Fibers — Few, small, and tender. Aroma — Very slight. Eating Quality — Very good. Flavor — Considered sweet and mildly acidic. The flavor is considered both pleasant and balanced. Juice — Moderate. Brix — About 13.5 degrees. This characteristic varies slightly with the number of fruit per tree; prevailing cultural practices; and the surrounding climatic conditions. Flesh Color — Pale yellow, (approximately RHS Yellow Group 11 B).

Stone:

*Type.*—Clingstone.

*Size.*—Considered medium large for the variety.

*Length.*—Average, about 26.0 to about 28.0 millimeters.

*Width.*—Average, about 23.0 to about 25.0 millimeters.

*Diameter.*—Average, about 15.0 to about 19.0 millimeters.

*Form.*—Obovoid.

*Base.*—The stone is usually rounded, but may vary from rounded, to straight.

*Apex.*—Shape — The stone apex is raised, and has an acute, short tip.

*Stone surface.*—Surface Texture — Irregularly furrowed toward the apex, and pitted toward the base. The stone exhibits substantial pitting laterally. Substantial grooving over the apical shoulders is evident. Surface pitting is prominent generally, and more frequently, it is present basally. Ridges — The surface texture varies from sharp to rounded. Ventral Edge — Width — Considered medium, and having a dimension of approximately 2.0 to about 3.5 millimeters at the mid-suture. The wings are most prominent over the suture line. Dorsal Edge — Shape — Full, heavily grooved, and having jagged edges. The dorsal edge is moderately eroded over the apical shoulder.

*Stone color.*—The color of the dry stone is an orange-white, (approximately RHS Orange White 159 C).

*Tendency to split.*—Occasional splitting has been noted.

*Kernel.*—Form — Kernel is gelatinous and immature when the fruit is fully mature. Texture — Shriveled. Pellicle — Pubescence not developed at fruit senescence. Color — (RHS Greyed Orange Group 164 C).

*Use.*—The subject variety 'Burnectten' is considered to be a Nectarine tree of the early season of maturity, and which produces fruit which are considered firm, attractively colored, and which are useful for both local and long distance shipping.

*Keeping quality.*—Excellent. Fruit has stored well up to 21 days after harvest at about 1.0 degree Celsius.

*Shipping quality.*—Good. Fruit showed minimal bruising of the flesh or skin damage after being subjected to normal harvesting and packing procedures.

*Resistance to insects and disease.*—No particular susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety of nectarine tree, what we claim is new and desire to secure by Plant Letters Patent is:

1. A new distinct variety of nectarine tree substantially as illustrated and described, and which is characterized principally as to novelty by producing an attractively colored yellow-fleshed, clingstone nectarine which is mature for harvesting and shipment approximately May 5 to May 11 under the ecological conditions prevailing in the San Joaquin Valley of Central California.

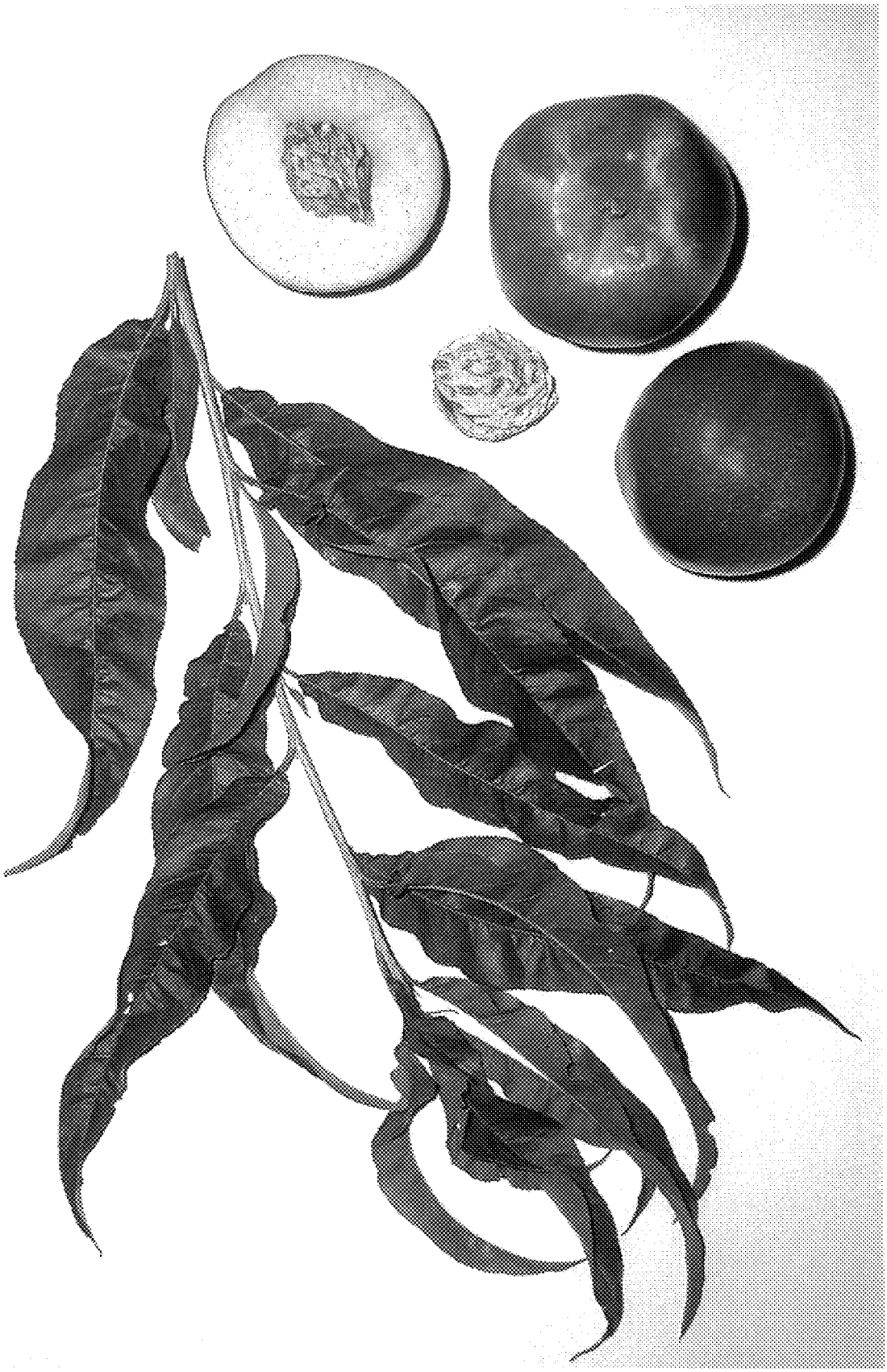

* * * * *